United States Patent
Palmer

(10) Patent No.: US 10,814,097 B2
(45) Date of Patent: *Oct. 27, 2020

(54) PACKAGED URINARY CATHETER WITH DISPENSING DEVICE

(71) Applicant: Cure Medical, LLC, Newport Beach, CA (US)

(72) Inventor: Timothy Palmer, Stillwater, MN (US)

(73) Assignee: Cure Medical, LLC, Newport Beach, CA (US)

( * ) Notice: Subject to any disclaimer, the term of this patent is extended or adjusted under 35 U.S.C. 154(b) by 662 days.

This patent is subject to a terminal disclaimer.

(21) Appl. No.: 15/671,341

(22) Filed: Aug. 8, 2017

(65) Prior Publication Data

US 2019/0046766 A1  Feb. 14, 2019

(51) Int. Cl.
*A61M 25/01* (2006.01)
*A61M 25/00* (2006.01)
*A61M 27/00* (2006.01)

(52) U.S. Cl.
CPC ...... *A61M 25/0113* (2013.01); *A61M 25/002* (2013.01); *A61M 25/0111* (2013.01); *A61M 25/0136* (2013.01); *A61M 27/00* (2013.01); *A61M 2210/1085* (2013.01)

(58) Field of Classification Search
CPC .......... A61M 25/0113; A61M 25/0111; A61M 27/00; A61M 25/0136; A61M 25/002; A61M 2210/1085
See application file for complete search history.

(56) References Cited

U.S. PATENT DOCUMENTS

| | | |
|---|---|---|
| 836,303 A | 11/1906 | Christensen |
| 1,206,655 A | 11/1916 | Belcher |
| 2,131,956 A | 10/1938 | Jones |
| 2,221,801 A | 11/1940 | Keppinger |
| 2,422,891 A | 6/1947 | Dickson |
| 2,584,644 A | 2/1952 | Verdi |
| 1,894,119 A | 7/1959 | Stenger |
| 3,365,761 A | 1/1968 | Kalvig |
| 4,140,127 A | 2/1979 | Cianci et al. |
| 4,141,452 A | 2/1979 | Martin et al. |
| 4,230,115 A | 10/1980 | Walz, Jr. et al. |
| 4,451,256 A | 5/1984 | Weikl et al. |
| 4,811,847 A | 3/1989 | Reif et al. |
| 5,108,066 A | 4/1992 | Lundstrom |
| 5,224,681 A | 7/1993 | Lundstrom |
| D358,679 S | 5/1995 | Garrity |
| 5,454,798 A | 10/1995 | Kubalak et al. |
| 5,529,148 A | 6/1996 | O'Leary |
| 5,603,702 A | 2/1997 | Smith et al. |
| 5,690,645 A | 11/1997 | Van Erp |
| 5,993,437 A | 11/1999 | Raoz |
| 6,004,305 A | 12/1999 | Hursman et al. |

(Continued)

*Primary Examiner* — Tatyana Zalukaeva
*Assistant Examiner* — Jessica R Arble
(74) *Attorney, Agent, or Firm* — SoCal IP Law Group LLP; Guy Cumberbatch; Steven C. Sereboff

(57) ABSTRACT

A packaged catheter equipped with a dispensing device and method of dispensing a packaged catheter using the dispensing device. The dispensing device is a pair of separately translatable movement control devices, each operably engaging the catheter for permitting unidirectional movement of the catheter in a first axial direction relative to the movement control devices.

15 Claims, 9 Drawing Sheets

(56) References Cited

U.S. PATENT DOCUMENTS

| | | |
|---|---|---|
| 6,010,105 A | 1/2000 | Davis |
| 6,053,905 A | 4/2000 | Daignault, Jr. et al. |
| 6,179,514 B1 | 1/2001 | Cheng |
| 6,402,726 B1 | 6/2002 | Genese |
| 6,427,964 B1 | 8/2002 | Hillstrom et al. |
| 6,578,709 B1 | 6/2003 | Kavanagh et al. |
| 7,094,220 B2 | 8/2006 | Tanghoj et al. |
| 7,458,964 B2 | 12/2008 | Mosler et al. |
| 7,476,223 B2 | 1/2009 | McBride |
| 7,985,217 B2 | 7/2011 | Mosler et al. |
| 8,734,426 B2 | 5/2014 | Ahmed et al. |
| 9,707,375 B2 | 7/2017 | Conway et al. |
| 9,782,563 B2 | 10/2017 | Palmer |
| 9,884,167 B2 | 2/2018 | Gustavsson |
| 10,099,032 B2 | 10/2018 | Gustavsson et al. |
| 10,315,008 B2 * | 6/2019 | Palmer ................ A61M 25/002 |
| 2003/0050653 A1 | 3/2003 | Berger |
| 2007/0073222 A1 | 3/2007 | Lilley, Jr. et al. |
| 2007/0088330 A1 | 4/2007 | House |
| 2007/0225649 A1 | 9/2007 | House |
| 2008/0103464 A1 * | 5/2008 | Mosler ................ A61M 25/0111 |
| | | 604/349 |
| 2012/0168324 A1 | 7/2012 | Carleo |
| 2012/0239005 A1 | 9/2012 | Conway et al. |
| 2013/0144271 A1 | 6/2013 | Passadore et al. |
| 2014/0257250 A1 | 9/2014 | Palmer |
| 2014/0277333 A1 * | 9/2014 | Lewis .................... A61B 34/30 |
| | | 623/1.11 |
| 2015/0352324 A1 | 12/2015 | Palmer |
| 2016/0193443 A1 * | 7/2016 | Palmer ................ A61M 25/002 |
| | | 206/210 |

\* cited by examiner

PACKAGED URINARY CATHETER WITH DISPENSING DEVICE

BACKGROUND

Intermittent catheters are typically used by patients suffering from urinary incontinence or by individuals unable to have voluntary urination. In our highly mobile culture, the ability to have the freedom to leave home for the day or longer is an important part of life. To accommodate this need single use catheters have been developed to allow patients to perform self catheterization. To aid in the insertion of the catheter in a body cavity they are often lubricated making the handling of the catheter difficult and messy. Many catheter packages are now designed to aid in the use of the catheter and at least the funnel end of the catheter is retained in the package. This allows the user to use the package to manipulate the catheter and avoid the messy and possible insanitary handling of the actual catheter. Manipulating a slippery catheter through a plastic bag can be quite difficult even for someone with excellent dexterity. To aid in the manipulation of the catheter various devices have been conceived to assist in movement of the catheter into and out of its package.

One such device is disclosed in U.S. Pat. No. 7,458,964 to Mosler et al. Mosler et al. discloses a catheter movement control device in which the catheter passes through a locking ring retained within the passage of a housing wherein the locking ring can be tilted within the passageway as between an aligned position for allowing passage of the catheter through the passage when the catheter is translated through the passage in a first direction, and a misaligned position for resisting passage of the catheter through the passage when the catheter is translated through the passage in a second opposite direction.

The movement control device of Mosler et al. aids in dispensing of a packaged catheter, but is difficult and cumbersome to use. Dispensing of a packaged catheter equipped with the movement control device of Mosler et al. requires the user to hold the movement control device with one hand while using the other hand to grip the lubricated catheter through the packaging, typically by pinching the catheter with the thumb against the pointer and/or index finger, and push the catheter towards and through the movement control device. Gripping and pushing of a lubricated catheter through packaging is challenging, and particularly challenging for the elderly and the infirm who are the very people who tend to use urinary catheters.

Accordingly, a substantial need continues to exist for a device capable of facilitating and simplifying dispensing of a packaged catheter.

SUMMARY OF THE INVENTION

A first aspect of the invention is a packaged catheter equipped with a dispensing device. A first embodiment of the first aspect of the invention includes (i) packaging defining a product retention chamber, (ii) a catheter defining a longitudinal axis retained within the product retention chamber, and (iii) a pair of separately translatable movement control devices, each operably engaging the catheter for permitting unidirectional movement of the catheter in a first axial direction relative to the movement control devices.

A second embodiment of the first aspect of the invention includes (i) packaging defining a product retention chamber, (ii) a catheter retained within the product retention chamber and defining an insertion end, a fixture end and a longitudinal axis, and (iii) first and second separately translatable movement control devices, each operably engaging the catheter for permitting unidirectional movement of the catheter in a first axial direction relative to the movement control devices, wherein (a) pulling the movement control devices away from one another along the longitudinal axis of the catheter effects longitudinal translation of the first movement control device in a second axial direction opposite the first axial direction along the longitudinal length of the catheter with inconsequential longitudinal translation of the second movement control device along the longitudinal length of the catheter, and (b) pushing the longitudinally separated movement control devices towards one another along the longitudinal axis of the catheter effects longitudinal translation of the second movement control device in the second axial direction along the longitudinal length of the catheter with inconsequential longitudinal translation of the first movement control device along the longitudinal length of the catheter.

The first aspect of the invention can optionally be equipped with a handle grip that includes at least (i) a hand graspable casing fixedly attached to one of the movement control devices, and (ii) a finger actuable element reciprocally engaged to the casing and fixedly attached to the other movement control device, wherein reciprocation of the finger actuable element relative to the casing effects pulling apart and pushing together of the movement control devices along the longitudinal axis of the catheter so as to effect dispensing of the catheter from the packaging.

A second aspect of the invention is a method of dispensing a catheter from a packaged catheter in accordance with the first aspect of the invention wherein the movement control devices permit unidirectional movement of the catheter in a first axial direction relative to the movement control devices. A first embodiment of the second aspect of the invention includes the steps of (i) pulling the pair of movement control devices away from one another along the longitudinal axis of the catheter so as to effect longitudinal translation of a first movement control device in a second axial direction opposite the first axial direction along the longitudinal length of the catheter with inconsequential longitudinal translation of the second movement control device along the longitudinal length of the catheter, and (ii) pushing the longitudinally separated movement control devices towards one another along the longitudinal axis of the catheter so as to effect longitudinal translation of the second movement control device in the second axial direction along the longitudinal length of the catheter with inconsequential longitudinal translation of the first movement control device along the longitudinal length of the catheter, whereby (iii) pushing of the longitudinally separated movement control devices towards one another along the longitudinal axis of the catheter effects dispensing of the catheter out of the packaging.

A second embodiment of the second aspect of the invention pertains to dispensing a catheter from a packaged catheter in accordance with the first aspect of the invention which is equipped with a handle grip, and includes the steps of (i) grasping the casing of the handle grip with a first hand, and (ii) reciprocating the button along a path with a finger on the first hand, wherein (a) movement of the button in one direction along the path effects a pulling movement of the pair of movement control devices away from one another along the longitudinal axis of the catheter so as to effect longitudinal translation of a first movement control device in a second axial direction opposite the first axial direction along the longitudinal length of the catheter with inconsequential longitudinal translation of the second movement control device along the longitudinal length of the catheter, and (b) movement of the button in the other opposite direction along the path effects a pushing movement of the pair of movement control devices towards one another along the longitudinal axis of the catheter so as to effect longitudinal translation of the second movement control device in the second axial direction along the longitudinal length of the catheter with inconsequential longitudinal translation of the first movement control device along the longitudinal length of the catheter, effecting a dispensing of the catheter out of the packaging.

DETAILED DESCRIPTION OF A PREFERRED EMBODIMENT

Nomenclature

10 Packaged Catheter
20 Packaging
21 First Longitudinal End of Packaging
22 Second Longitudinal End of Packaging
29 Product Retention Chamber
30 Dispensing Device
31 First Movement Control Device
32 Second Movement Control Device
40 Main Body of Each Movement Control Device
$40_1$ First Portion of Main Body of Each Movement Control Device
$40_2$ Second Portion of Main Body of Each Movement Control Device
$40_{LA}$ Longitudinal Axis of Main Body
41 First Longitudinal End of Main Body
42 Second Longitudinal End of Main Body
43 Engagement Members
$43_1$ First Longitudinally Extending Engagement Member
$43_2$ Second Longitudinally Extending Engagement Member
45 Cap or Seal
49 Passageway Through Main Body
49i Interior End (Opening) of Passageway Through Main Body
49e Exterior End (Opening) of Passageway Through Main Body
$49_{CA}$ Central Axis of Passageway
50 Locking Member of Each Movement Control Device
51 First or One Lateral End of Locking Member
52 Second or Other Lateral End of Locking Member
55 Hinge
$55_P$ Hinge Pivot Axis
59 Orifice Though Locking Member
$59_{CA}$ Central Axis of Orifice
60 Catheter
61 Lumen or Insertion End
62 Funnel or Fixture End
$69_{CA}$ Longitudinal Central Axis of Catheter
$69_{x1}$ First Axial Longitudinal Direction
$69_{x2}$ Second Axial Longitudinal Direction
70 Handle Grip
71 Casing of Handle Grip
72 Activation Element or Button on Handle Grip
$72_P$ Path of Movement of Activation Element or Button
80 Release Actuator Element
90 Handle Opening in Packaging
X Longitudinal Direction
Y Lateral Direction
Z Transverse Direction Definitions As utilized herein, including the claims, the term "inconsequential", when used to describe longitudinal translation of a movement control device along the longitudinal length of a catheter, means a distance of less than 1 cm.

DESCRIPTION

Construction

Figure 1:
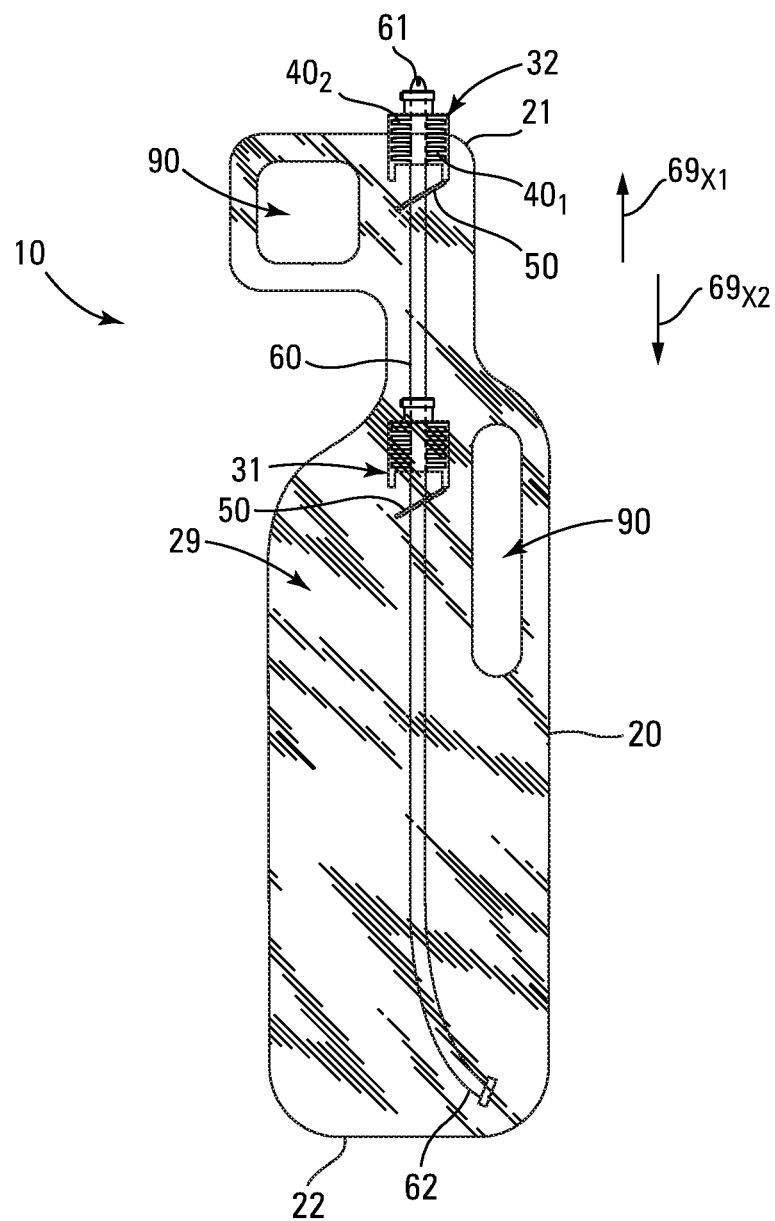
FIG. 1 is a front view of one embodiment of a packaged catheter in accordance with this invention, depicting the movement control members of the dispensing device pulled apart in a longitudinally spaced relationship and the catheter fully retained within the packaging.
Figure 2:
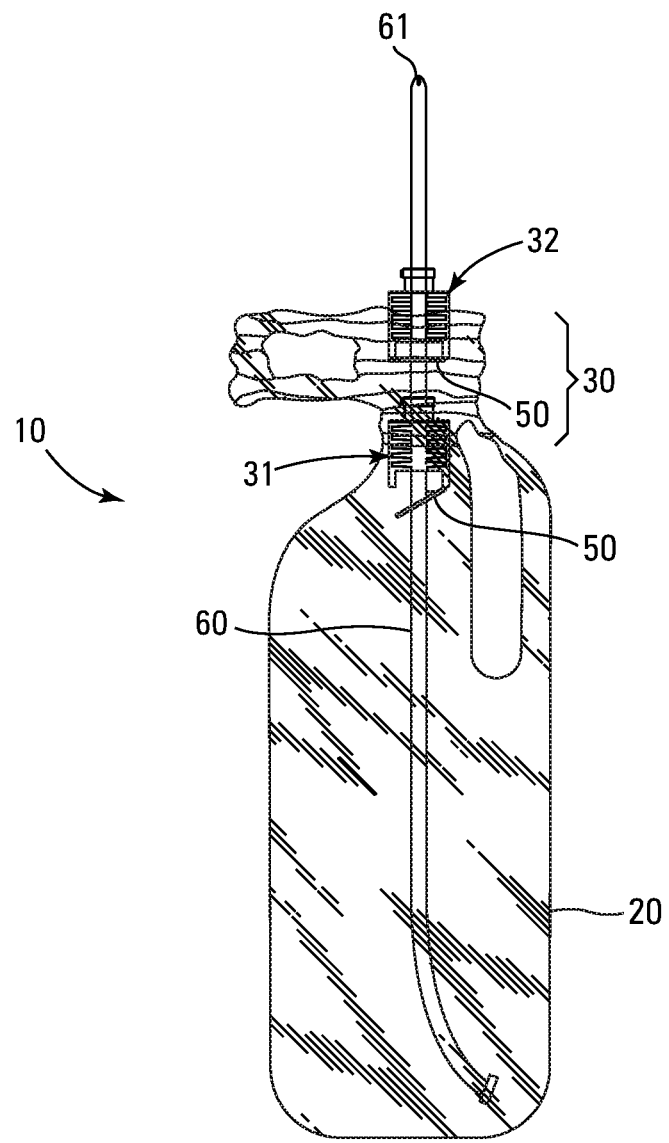
FIG. 2 is a front view of the invention depicted in FIG. 1 depicting the movement control members of the dispensing device pushed together and the catheter partially dispensed from the packaging.
Figure 3:
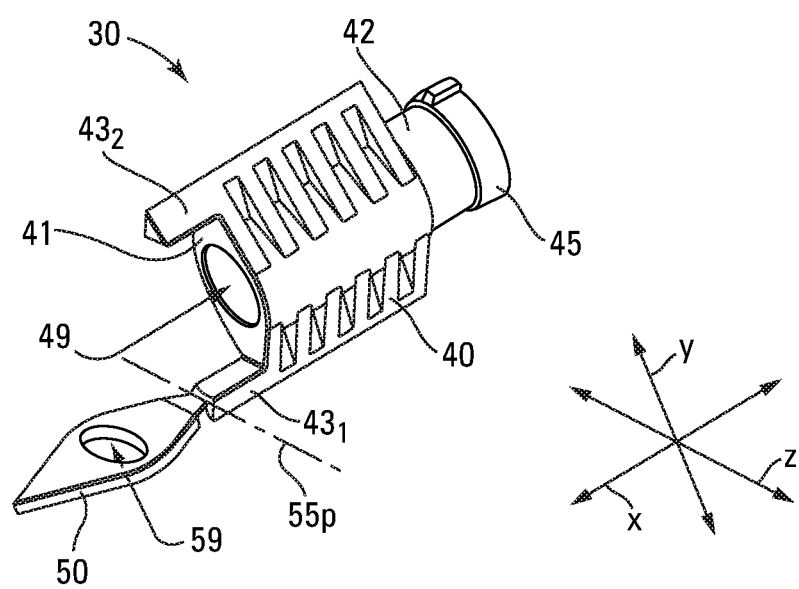
FIG. 3 is a perspective view of one of the movement control devices depicted in FIGS. 1 and 2 with the locking member pivoted into the second locking position.
Figure 4:
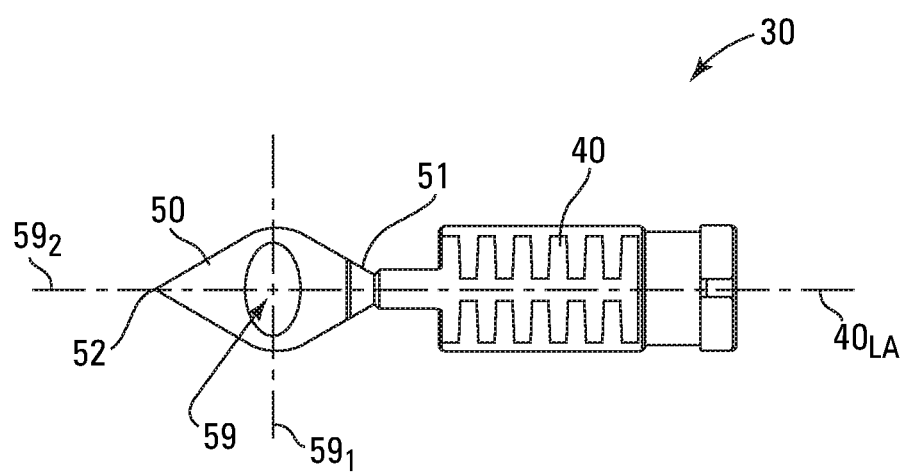
FIG. 4 is a side view of the catheter movement control device depicted in FIG. 3.
Figure 5:
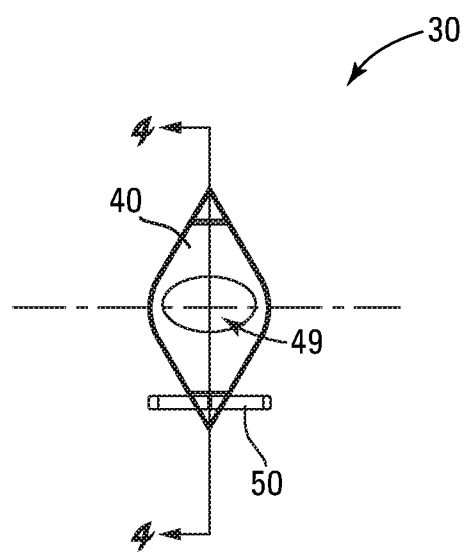
FIG. 5 is an end view of the catheter movement control device depicted in FIG. 3.
Figure 6:
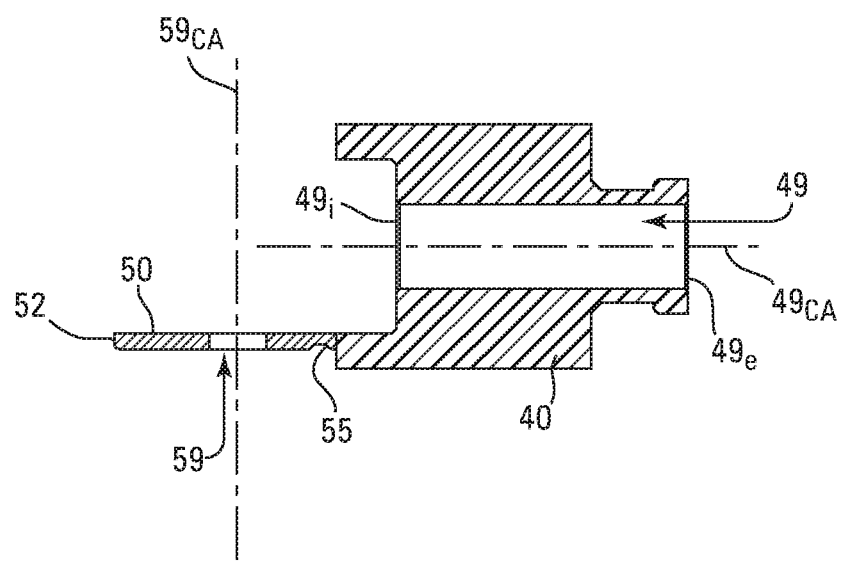
FIG. 6 is a cross-sectional side view of the catheter movement control device depicted in FIG. 3 taken along line 6-6.

Referring to FIGS. 1 and 2, the invention is a packaged catheter 10 equipped with a dispensing device 30.

Packaged Catheter

The packaged catheter 10 includes a catheter 60, such as an intermittent urinary catheter, retained within the product retention chamber 29 of a package 20. The catheter 60 defines an insertion end 61 and a fixture end 62, and a longitudinal central axis $69_{CA}$.

Catheter

The catheter 60 may have any desired longitudinal length and shape effective for achieving the function of eliminating urine from the bladder of a male or female patient. Preferably, the longitudinal length for an adult female catheter 60 is between 2-6 inches, the longitudinal length of the adult male catheter 60 is between 10-16 inches, and the longitudinal length of a pediatric catheter 60 is between 5-11 inches.

Packaging

The packaging 20 may be selected from any of the customary packaging used for catheters so long as the packaging is sufficiently supple and flexible that the packaging 20 does not prevent or inhibit translation of the movement control devices (31 and 32) towards and away from one another when gripped through the packaging 20.

Dispensing Device

The dispensing device 30 includes a pair of movement control devices (31 and 32) for facilitating longitudinal x movement of the catheter 60 from a second longitudinal end 22 of the packaging 20 towards a first longitudinal end 21 of the packaging 20 for controlled dispensing of the catheter 60 from the packaging 20.

The movement control devices (31 and 32) each operably engage the catheter 60 and are separately translatable along the longitudinal central axis $69_{CA}$ of the catheter 60 for permitting unidirectional movement of the catheter 60 in a first axial direction $69_{x1}$ relative to the movement control devices (31 and 32).

The unidirectional nature of the movement control devices (31 and 32) (i.e., ability of each movement control device (31 and 32) to slide along the longitudinal length of the catheter 60 in a second axial direction $69_{x2}$ coupled with an inability to slide along the longitudinal length of the catheter 60 in the opposite first axial direction $69_{x1}$ along the longitudinal length of the catheter 60), allows a paired set of the movement control device (31 and 32) to quickly, easily and controllably dispense a catheter 60 from a package 20 by repetitively pushing together and pulling apart the paired set of movement control device (31 and 32). Pulling the movement control devices (31 and 32) away from one another along the longitudinal length of the catheter 60 effects longitudinal translation of the first movement control device 31 along the longitudinal length of the catheter 60 in the second axial direction $69_{x2}$ with inconsequential longitudinal translation of the second movement control device 32 along the longitudinal length of the catheter 60, while pushing the longitudinally separated movement control devices (31 and 32) towards one another along the longitudinal length of the catheter 60 effects longitudinal translation of the second movement control device 32 in the second axial direction $69_{x2}$ with inconsequential longitudinal translation of the first movement control device 31 along the longitudinal length of the catheter 60.

The dispensing device 30 may further include a handle grip 70 for facilitating single handled dispensing of the catheter 60 from the packaging 20 using the dispensing device 30, a feature long sought by users.

Figure 8:
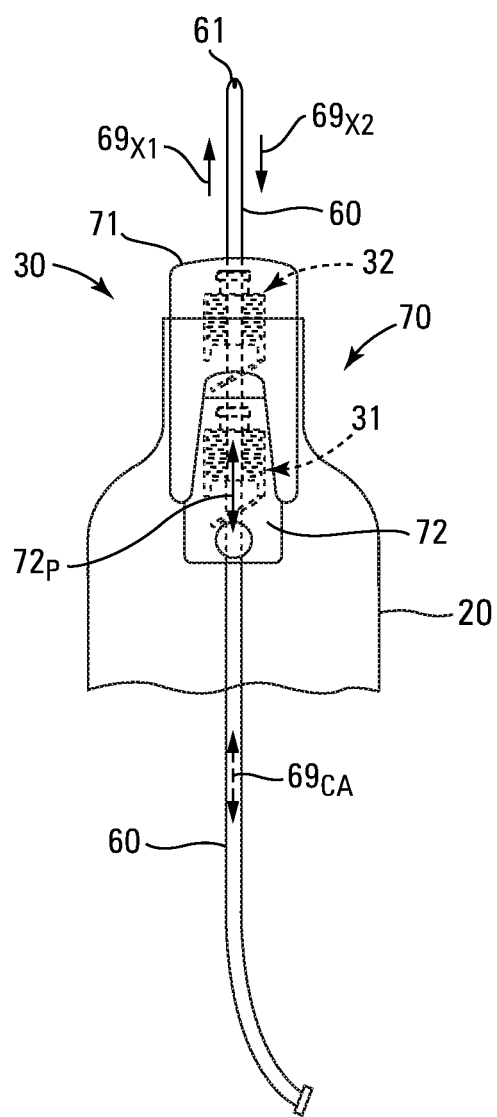
FIG. 8 is a front view of a portion of another embodiment of a packaged catheter in accordance with this invention schematically depicting a handle grip component for facilitating single-handed dispensing of the catheter.

FIG. 8 schematically depicts an exemplary handle grip 70. Referring to FIG. 8, the handle grip 70 includes a hand graspable casing 71, and a finger actuable element 72 reciprocally (i.e., telescoping) engaged to the casing 71 for travel along a path 72$p$ relative to the casing 71. The casing 71 and finger actuable element 72 are preferably sized, configured and arranged for thumb actuation of the finger actuable element 72 while cradling of the casing 71 within the palm of that hand. The casing 71 is fixedly attached to a second of the movement control devices 32, while the finger actuable element 72 is fixedly attached to a first of the movement control devices 31, whereby reciprocation of the finger actuable element 72 relative to the casing 71 along a path 72$p$ effects a pulling apart and pushing together of the movement control devices 31 and 32 along the longitudinal axis $69_{CA}$ of the catheter 60 so as to effect dispensing of the catheter 60 from the packaging 20.

The finger actuable element 72 may optionally be biased, such as by use of a spring, towards the pushed apart configuration to effect auto "reloading" of the dispensing device 30.

When the dispensing device 30 includes a handle grip 70, the packaging 20 can be conveniently heat sealed to the casing 71 with the finger actuable element 72 retained wholly within and actuated through the packaging 20.

Figure 9:
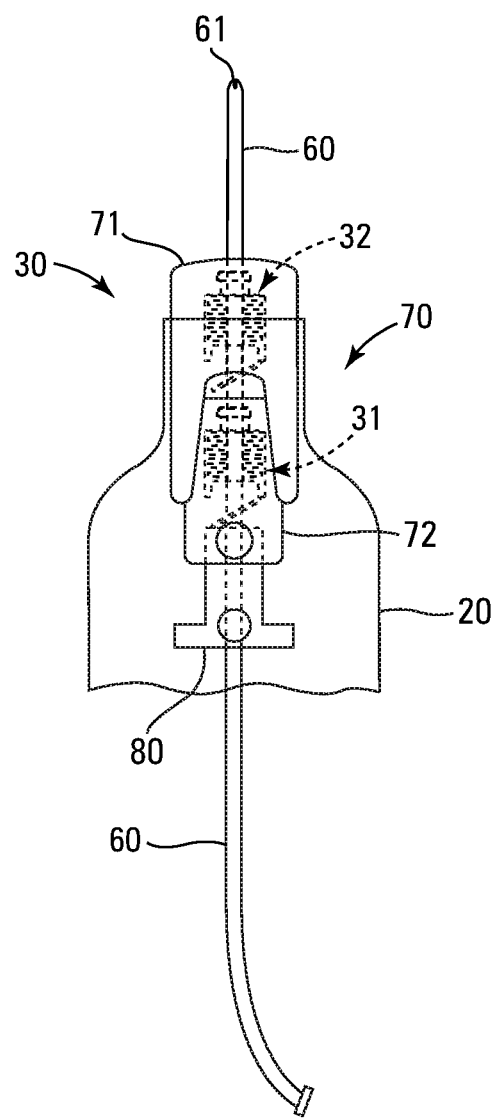
FIG. 9 is a front view of a portion of the handle grip component schematically depicted in FIG. 8, further equipped with a schematically depicted release element.

Referring to FIG. 9, a release actuator element 80 may optionally be provided for effecting selective manual sustained pivoting of the locking member 50 on the first movement control device 31 into the aligned positioned regardless of longitudinal movement of the catheter 60 relative to the first movement control device 31 for allowing movement of a dispensed catheter 60 in the second axial longitudinal direction $69_{x2}$ and back into the packaging 20 by actuating the release actuator element 80 when the first movement control device 31 is pushed against and pivoting the locking member 50 on the second movement control device 32 into the aligned positioned.

The release actuator element 80 may be telescopingly mounted onto the finger actuable element 72 for travel as between a first disengaged position with the release actuator element 80 spaced from the locking member 50 on the first movement control device 31 and a second engaged position with the release actuator element 80 contacting and pivoting the locking member 50 on the first movement control device 31 into an aligned positioned.

Movement Control Device

FIGS. 1-9, and in particular FIGS. 3-7, depict a preferred embodiment of a movement control device 30 suitable for use as the movement control devices (31 and 32).

This embodiment of the movement control device 30 has a main body 40 and a locking member 50 hingedly attached to the main body 40. The main body 40 and locking member 50 are preferably formed as a monolithic device with the locking member 50 pivoting about a live hinge 55 formed in the single piece device. The locking member 40 may be made from any suitable material, including various plastics such as polyethylene, polypropylene, polyvinyl chloride (PVC), and nylon.

The main body 40 of the movement control device 30 has a first longitudinal end 41 and a second longitudinal end 42, and defines a longitudinal axis $40_{LA}$. A passageway 49 extends through the main body 40 from an opening 49$i$ in the first longitudinal end 41 of the main body 40 to an opening 49$e$ in the second longitudinal end 42 of the main body 40. The passageway 49 is preferably linear and defines a central axis $49_{CA}$. The passageway 49 is sized and configured to allow passage of the lumen portion of a catheter 60.

Figure 7:
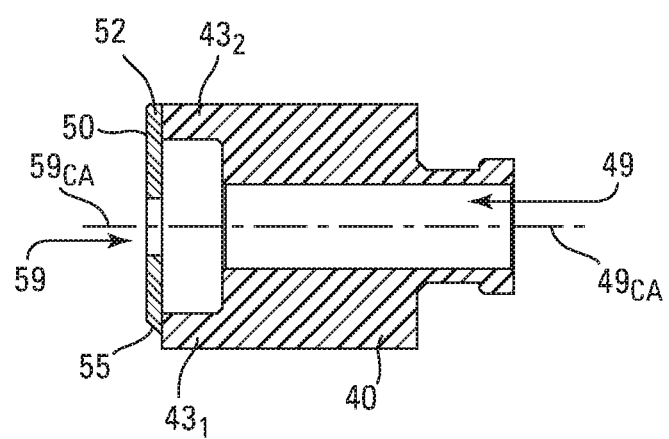
FIG. 7 is a cross-sectional side view of the catheter movement control device depicted in FIG. 3 taken along line 7-7, but with the locking mechanism pivoted into the first dispensing position.

A first lateral end 51 of the locking member 50 is hingedly attached to the main body 40 at hinge 55, permitting pivoting of the locking member 50 relative to the main body 40 about a hinge pivot axis 55$p$ as between a first aligned position depicted in FIG. 7, and a second misaligned position depicted in FIGS. 3-6. In the first aligned position the second lateral end 52 of the locking member 50 contacts the main body 40 and the central axis $59_{CA}$ of an orifice 59 through the locking member 50 is aligned with the central axis $49_{CA}$ of the passageway 49. When in the first aligned position a catheter 60 may be axially translated through the aligned orifice 59 and passageway 49. Pivoting of the locking member 50 from the first aligned position towards the second misaligned position pivots the second lateral end 52 of the locking member 50 away from the main body 40, resulting in an increasing misalignment of the central axis $59_{CA}$ of the orifice 59 and the central axis $49_{CA}$ of the passageway 49 until movement of a catheter 60 is inhibited through the misaligned orifice 59 and passageway 49.

In a preferred embodiment, laterally y spaced engagement members 43 extend longitudinally x from a longitudinal end of the main body 40, with a first lateral end 51 of the locking member 50 hingedly attached to a first $43_1$ of these engagement members 43 at hinge 55, and the second $43_2$ of these engagement members 43 located to contact the second lateral end 52 of the locking member 50 when the locking member 50 is in the first aligned position. The engagement members 43 provide a modest offset between the passageway 49 and the orifice 59 for avoiding severe bending and kinking of the catheter 60 when the central axis $59_{CA}$ of the orifice 59 and the central axis $49_{CA}$ of the passageway 49 are misaligned.

Pivoting of the locking member 50 about the hinge pivot axis 55p is effected by axial translation of the movement control device 30 along the longitudinal length of a catheter 60 passing through the passageway 49 and frictionally passing through the orifice 59 in the movement control device 30. Referring generally to FIGS. 1 and 2, axial translation of a movement control device 30 in the first longitudinal direction $69_{x1}$ along the length of a catheter 60 causes pivoting of the locking member 50 towards the second misaligned position so as to lock the movement control device 30 onto the catheter 60. When locked, any further movement of the movement control device 30 in the first longitudinal direction $69_{x1}$ will effect concomitant movement of the catheter 60 along with the movement control device 30 in the first longitudinal direction $69_{x1}$.

In contrast, axial translation of a movement control device 30 in the second longitudinal direction $69_{x2}$ along the length of a catheter 60 causes pivoting of the locking member 50 towards the first aligned position so as to unlock the movement control device 30 from the catheter 60. When unlocked, the movement control device 30 is free to travel along the longitudinal length of the catheter 60. Such freedom of travel can continue along the entire length of the catheter 60 in the second longitudinal direction $69_{x2}$, but will of course be promptly lost when the movement control device 30 is moved in the first longitudinal direction $69_{x1}$ as the locking member 50 will pivot into the second misaligned position and lock the movement control device 30 onto the catheter 60.

The size and dimensions of the movement control device 30 are generally dictated by the size of the catheter 60 with which it is used, but the main body 40 should be large enough to be retentively pinched between the thumb and index finger in order to allow dispensing of the catheter 60 from the packaging 20 through the movement control device 30. Dimensions of an exemplary movement control device 30 are provided in Table One below.

TABLE ONE (Exemplary Dimensions)

| DIMENSION | SIZE |
| --- | --- |
| Longitudinal Length of Main Body 40 | 25 mm |
| Lateral Width of Main Body 40 | 20 mm |
| Transverse Depth of Main Body 40 | 10 mm |
| Cross Sectional Area of Passageway 49 | 200 mm² |
| Thickness of Locking Member 50 | 1-2 mm |
| Cross Sectional Area of Orifice 59 | 100 mm² |

Referring to FIGS. 1 and 2, when incorporated into a packaged catheter 10 at least one of the movement control devices 31 and 32 is preferably fixedly attached to the packaging 20, with a first portion $40_1$ of the main body 40 positioned within the product retention chamber 29 defined by the packing 20, and a second portion $40_2$ of the main body 40 positioned exterior to the product retention chamber 29. The passageway 49 through the main body 40 of this affixed movement control device 32 provides a port through the packaging 20 from an interior end 49i of the passageway 49 to an exterior end 49e of the passageway 49. The affixed movement control device 32 can conveniently be heat sealed at a longitudinal end 21 of the packaging 20. A cap or seal 45 can be placed over the exterior end 49e of the passageway 49. The other movement control device 31 is preferably wholly located within the product retention chamber 29 of the packaging 20 and may also be fixedly attached to the packaging 20 so long as the packaging 20 is supple enough to allow the movement control devices 31 and 32 to be pushed together and pulled apart.

Use

The packaged intermittent urinary catheter 10 can be used by patients for self catheterization. Prior to use the patient should take all sanitary procedures advised by their doctors to decrease the risks of infection.

Referring to the embodiment depicted in FIGS. 1 and 2, first the seal or cap 45 is removed to open the port through the packaging 20 defined by the passageway 49 through the main body 40 of the second movement control device 32.

The user then grasps or pinches the main body 40 of the first movement control device 31 through the packaging 20 with one hand, grasps or pinches the main body 40 of the second movement control device 32 with the other hand through the packaging 20, and then repetitively pulls the movement control devices 31 and 32 apart as depicted in FIG. 1 to "load" the dispensing device 30 without effecting longitudinal movement of the catheter 60 relative to the second movement control device 31, and pushes the movement control devices 31 and 32 together as depicted in FIG. 2 to dispense a length of the catheter 60 from the package 20.

Referring to the embodiment depicted in FIGS. 8 and 9, the user cradles the casing 71 in the palm of a hand with the fingers wrapped around and gripping the casing 71 and the thumb of that same hand placed upon a pad on the activation element 72. The user then uses the thumb to reciprocate the activation element 72 relative to the casing 71 along the path of travel 72p, thereby pulling the movement control devices 31 and 32 apart without effecting longitudinal movement of the catheter 60 relative to the second movement control device 32 attached to the casing 71 when the activation element 72 is moved in one direction along the path 72p, and pushing the movement control devices 31 and 32 together to dispense a length of the catheter 60 from the package 20 when the activation element 72 is moved in the opposite direction along the path 72p.

Referring to FIGS. 1 and 2, two handed pushing and pulling of the movement control devices 31 and 32 to effect dispensing of a catheter 60 may be simplified by attaching both movement control devices 31 and 32 to the packaging 20 in longitudinally spaced relationship and providing a handle opening 90 proximate each movement control device 31 and 32.

Referring to FIGS. 8 and 9, one handed pushing and pulling of the movement control devices 31 and 32 to effect dispensing of a catheter 60 may be simplified by including the handle grip 70 feature.

The dispensing device 30 also functions to preventing the fixture end 62 of the catheter 60 from advancing out of the package 20.

I claim:

1. A packaged catheter equipped with a dispensing device, comprising:
   (a) packaging defining a product retention chamber,
   (b) a catheter defining a longitudinal axis retained within the product retention chamber,
   (c) a pair of movement control devices separately translatable with respect to each other along the catheter, one of which is retained within the product retention chamber, each operably engaging the catheter for permitting unidirectional movement of the catheter in a first axial direction relative to the movement control devices, and
(d) a handle grip that includes at least (i) a hand graspable casing fixedly attached to one of the movement control devices, and (ii) a finger actuable element reciprocally engaged to the casing and fixedly attached to the other movement control device, wherein reciprocation of the element relative to the casing effects pulling apart and pushing together of the movement control devices along the longitudinal axis of the catheter so as to effect dispensing of the catheter from the packaging.

2. The packaged catheter of claim 1 wherein the packaging is heat sealed to the casing with the finger actuable element retained wholly within and actuated through the packaging.

3. The packaged catheter of claim 1 further comprising a manually actuable release element in operable engagement with the other movement control device for converting the other movement control device from a unidirectional movement control device to a bidirectional movement control device when the release element is actuated.

4. The packaged catheter of claim 1 wherein the packaging is supple and at least one of the movement control devices is attached to the packaging.

5. The packaged catheter of claim 1 wherein:
(a) each movement control device comprises (i) a main body having a passageway defining a central axis, and (ii) a locking member hingedly attached to the main body for pivoting about a pivot axis and having an orifice defining a central axis extending there through, (iii) whereby the locking member is pivotable about the pivot axis relative to the main body as between a first position wherein the central axis of the orifice is aligned with the central axis of the passageway, and a second position wherein the central axis of the orifice is misaligned with the central axis of the passageway, and
(b) the catheter extends through the passageway and the orifice in both of the movement control devices.

6. The packaged catheter of claim 5 further comprising a manually actuable release element in operable engagement with the locking member of the other movement control device for pivoting the locking member of the other movement control device into the first position upon actuation whereby the central axis of the orifice through the locking member of the other movement control device is aligned with the central axis of the passageway through the main body of the other movement control device such that the other movement control device is converted from a unidirectional movement control device to a bidirectional movement control device when the release element is actuated.

7. The packaged catheter of claim 5 wherein the locking member is planar.

8. The packaged catheter of claim 1 wherein the catheter is an intermittent urinary catheter.

9. The packaged catheter of claim 1 wherein the finger actuable element and thus the other of the movement control devices is biased by a spring towards a pulled apart configuration of the two movement control devices.

10. A packaged catheter equipped with a dispensing device, comprising:
(a) packaging defining a product retention chamber,
(b) a catheter defining an insertion end, a fixture end and a longitudinal axis, retained within the product retention chamber, and
(c) first and second movement control devices separately translatable with respect to each other along the catheter, one of which is retained within the product retention chamber, each operably engaging the catheter for permitting unidirectional movement of the catheter in a first axial direction relative to the movement control devices, wherein (i) pulling the movement control devices away from one another along the longitudinal axis of the catheter effects longitudinal translation of the first movement control device in a second axial direction opposite the first axial direction along the longitudinal length of the catheter with inconsequential longitudinal translation of the second movement control device along the longitudinal length of the catheter, and (ii) pushing the longitudinally separated movement control devices towards one another along the longitudinal axis of the catheter effects longitudinal translation of the second movement control device in the second axial direction along the longitudinal length of the catheter with inconsequential longitudinal translation of the first movement control device along the longitudinal length of the catheter, wherein:
each of the first and second movement control devices comprise:
(i) a main body having:
(1) longitudinally spaced opposed first and second ends,
(2) a passageway through the main body extending between an opening in the first end of the main body and an opening in the second end of the main body, and
(3) first and second laterally spaced engagement members extending longitudinally from the first end of the main body, the engagement members positioned on diametric sides of the opening in the first end of the main body, and
(ii) a locking member hingedly attached at a first lateral end to the first engagement member for pivoting about a pivot axis, the locking member having an orifice there through,
wherein the catheter extends through and is frictionally engaged within the orifice for effecting pivoting of the locking member about the pivot axis upon translational movement of the catheter along the central axis of the catheter as between a first position wherein the locking member contacts the second engagement member with the central axis of orifice aligned with the interior end of the central axis of the port for accommodating passage of the catheter through the orifice, and a second position wherein the central axis of the orifice is misaligned with the interior end of the central axis of the port so as to inhibit passage of the catheter through the orifice.

11. The packaged catheter of claim 10 further comprising a handle grip that includes at least (i) a hand graspable casing fixedly attached to one of the movement control devices, and (ii) a finger actuable button reciprocally engaged to the casing and fixedly attached to the other movement control device, wherein reciprocation of the button relative to the casing effects the pulling apart and pushing together of the movement control devices along the longitudinal axis of the catheter so as to effect dispensing of the catheter from the packaging.

12. The packaged catheter of claim 10 wherein the first movement control device is closer to the fixture end of the catheter than then second movement control device, whereby the first axial direction is towards the insertion end of the catheter.

13. The packaged catheter of claim 10 wherein the packaging is supple and both movement control devices are attached to the packaging.

14. The packaged catheter of claim 10 further comprising a manually actuable release element in operable engagement with the second movement control device for converting the second movement control device from a unidirectional movement control device to a bidirectional movement control device when the release element is actuated.

15. The packaged catheter of claim 10 wherein the second movement control device is disposed at and attached to one end of the packaging with the first end of the second movement control disposed inside the product retention chamber and the second end of the second movement control disposed outside the product retention chamber, whereby the passageway through the main body of the second movement control device defines a port through which the catheter retained within the product retention chamber of the packaging may be dispensed from the packaging.

\* \* \* \* \*